(12) United States Patent
Kurdyumov et al.

(10) Patent No.: US 8,475,843 B2
(45) Date of Patent: Jul. 2, 2013

(54) SILYL ETHER-MODIFIED HYDROPHILIC POLYMERS AND USES FOR MEDICAL ARTICLES

(75) Inventors: Aleksey V. Kurdyumov, Maplewood, MN (US); Robert Hergenrother, Eden Prairie, MN (US); Bruce M. Jelle, Chanhassen, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

(21) Appl. No.: 12/981,885

(22) Filed: Dec. 30, 2010

(65) Prior Publication Data

US 2011/0159101 A1 Jun. 30, 2011
US 2012/0052123 A9 Mar. 1, 2012

Related U.S. Application Data

(60) Provisional application No. 61/291,640, filed on Dec. 31, 2009.

(51) Int. Cl.
*A61K 9/02* (2006.01)
*A61F 2/02* (2006.01)
*A61L 27/00* (2006.01)

(52) U.S. Cl.
USPC .............................. 424/486; 424/426; 427/2.1

(58) Field of Classification Search
None
See application file for complete search history.

(56) References Cited

U.S. PATENT DOCUMENTS

2003/0215649 A1* 11/2003 Jelle .............................. 428/447
2004/0208985 A1* 10/2004 Rowan et al. ................ 427/2.25
2007/0087025 A1 4/2007 Fitzhugh et al.

FOREIGN PATENT DOCUMENTS

WO 03/055611 7/2003

OTHER PUBLICATIONS

PCT Search Report for International Application No. PCT/US2010/062489; mailed on Apr. 28, 2011.

* cited by examiner

*Primary Examiner* — Robert A Wax
*Assistant Examiner* — Sarah Park
(74) *Attorney, Agent, or Firm* — Kagan Binder, PLLC

(57) ABSTRACT

Silane-functionalized hydrophilic polymers and polymeric matrices are described. Hydrophilic matrices can be formed from the polymers, and can be used in association with the preparation of implantable and injectable medical devices. Exemplary devices include those having a durable lubricious coating formed from the hydrophilic polymers.

18 Claims, No Drawings

SILYL ETHER-MODIFIED HYDROPHILIC POLYMERS AND USES FOR MEDICAL ARTICLES

PRIORITY CLAIM

This application claims the benefit of U.S. Provisional Patent Application Ser. No. 61/291,640, filed Dec. 31, 2009, entitled SILYL ETHER-MODIFIED HYDROPHILIC POLYMERS, the disclosure of which is incorporated herein by reference.

TECHNICAL FIELD

The present invention relates to hydrophilic polymers having pendent silyl ether-containing groups. The invention also relates to polymeric matrices formed from these polymers, which can be used in association with an implantable or insertable medical device.

BACKGROUND

Surface coatings can provide medical articles, such as those that are implanted or temporarily inserted into the body, with a variety of distinct benefits. These benefits include lubricity and wettability, passivity against protein absorption, antimicrobial properties, drug delivery, biocompatibility and hemocompatibility. The demand for medical articles having these types of coatings is rapidly increasing because they generally improve the function of the device upon implantation or insertion in the body. However, while these properties can provide clear advantages for the function of these devices, the preparation of these coatings can, in many cases, be technically challenging and also quite costly.

Medical articles are typically prepared from plastic or metal biomaterials, or combinations of these biomaterials. Generally, plastic medical articles provide good substrates for the bonding and immobilization of coating materials, as the plastic surface can be reacted with chemical groups that are provided with the coating material. On the other hand, the immobilization of coating materials on metal substrates is generally more challenging because, in many cases, the metal surface is not able to directly covalently bond the reactive group. To overcome this, a base layer of material, often called a "priming layer" or a "tie layer", is disposed on the surface to provide a material to which a subsequent coating material can react. Therefore, many metal-containing medical articles having coatings include two or more coated layers, at least one of which is a base layer that facilitates the immobilization of materials of a second layer.

To maintain the integrity of the coating, the material of the base layer should remain continuously contacted with the metal surface of the device after the coating is formed and during use of the coated device. Problems with the coating may be seen if a portion of the coated base layer separates from the surface, which can result in delamination of all or portions of the coated materials from the surface of the device. As a result, surface properties may be lost before or during use, for example, before or during implantation or insertion into the body.

For some medical articles which are flexed or bent during use, the material of the base layer should be compliant. A compliant base layer can prevent the coating from cracking or delaminating.

Parylene™ (poly(para-xylylene)) is commonly used as a base layer material. Parylene™ base layers are typically very thin (0.1 micron to 75 microns), continuous, inert, transparent, and conformal films. Parylene™ is applied to substrates in an evacuated deposition chamber by a process known as vapor deposition polymerization (VDP). This involves the spontaneous resublimation of a vapor that has been formed by heating di-para-xylylene, which is a white crystalline powder, at approximately 150° C., in a first reaction zone. The vapor resulting from this preliminary heating is then cleaved molecularly, or pyrolyzed, in a second zone at 650° C. to 700° C. to form para-xylylene, a very reactive monomer gas. This monomer gas is introduced to the deposition chamber, where it resublimates and polymerizes on substrates at room temperature and forms a transparent film. In the final stage, para-xylylene polymerizes spontaneously onto the surface of objects being coated. The coating grows as a conformal film (poly-para-xylylene) on all exposed substrate surfaces, edges and in crevices, at a predictable rate. Parylene™ formation is spontaneous, and no catalyst is necessary.

While the benefits of a Parylene™ base layer can be clearly seen, there are various drawbacks to using this process in coating processes for metal medical articles wherein a base or tie layer is needed to form a coating. For example, as indicated above, the process of Parylene™ deposition is rather involved and furthermore requires the use of costly apparatus to carry out the vapor deposition process. Also, in order to ensure that an adequate Parylene™ layer is formed on the surface of the device substrate, it is typically necessary to thoroughly remove oils and contaminants from the device surface. This can add time to the coating process and also subjects the coated article to potential defects in the coating if it not cleaned adequately. Furthermore, in order to promote sufficient adhesion between the device surface and Parylene™ layer, the surface of the metal article typically needs to be pretreated with a silane material. This, again, can add time and expense to the coating process. Another approach is to apply fluorinated materials such as Teflon™ to the metal surface. These coatings, however, can be excessively thick, have relatively low adhesion and elasticity, and can crack under stress.

Another challenge for providing coatings relates to those implantable devices that are more complex in terms of geometry. For example, small implantable medical devices, such as stents, often have intricate geometries. In some cases, when these medical devices having intricate geometries are subjected to a coating procedure, webbing or bridging of the coating solution may occur, resulting in a coating that hinders the device from functioning properly. Other coating reagents and techniques utilize light to fix the coating compound on the device surface. However, methods involving light activation can potentially be inadequate for providing uniform coatings over the entire surface of the device. In particular, inner surfaces of devices can be difficult to access with an activating amount of light.

SUMMARY

The present invention is related to hydrophilic polymers having reactive silyl ether chemistries ("silyl ether-modified hydrophilic polymers") and use of these polymers for the formation of polymeric matrices. The polymeric matrices can be used in association with an implantable or insertable medical device, such as a coating on the surface of a device. The silyl ether-modified hydrophilic polymers can also be formed into articles such as gels, crosslinked matrices, or pellets, and these can be used for a medical purpose.

For example, for a coating, silyl ether groups can be hydrolyzed and reacted to a target chemical moiety on a device, causing covalent attachment of the hydrophilic polymer to a surface. Alternatively, or in addition, the silyl ether groups can be hydrolyzed and reacted to bond to another polymer, so that a crosslinked polymeric network forms. The other polymer can be another silyl ether-modified hydrophilic polymer, or a different hydrophilic polymer, such as one that includes one or more silyl ether reactive groups (e.g., hydroxyl, amine). The covalent bonding increases the durability of the polymeric matrix. When in the form of a coating, the polymeric material can remain more stably attached to the surface.

Experimental studies associated with the current invention demonstrate that the silyl ether-modified hydrophilic polymer was also able to form a durable and lubricious coating on a variety of substrate materials. In some aspects, the silyl ether-modified hydrophilic polymer is in conjunction with implantable or insertable medical devices formed partially or entirely of a metal or a glass. The silyl ether group can be activated to covalently bond directly with a metal or glass surface. The direct bonding can eliminate the need for a polymeric tie layer which may otherwise be required to form a lubricious coating. As such, coating properties can be improved (e.g., the coating may be thinner than those formed of multiple layers of different polymeric materials), and less material may be required to form the coating. This can result in improvements in biocompatibility, as well as provide an economic advantage. The silyl ether-modified hydrophilic polymer was also able to form a durable and lubricious coating when applied to and heated on plastic substrates.

Use of the silyl ether-modified hydrophilic polymer can also be advantageous for those devices having a complex geometry of having inner surfaces, such as an inner lumen. Some reactive chemistries used for coating medical devices require light activation to cause a covalent bonding for association of a polymeric material on a surface. Some medical devices have surfaces which are difficult to irradiate, and therefore coating these surfaces with traditional materials may not allow a suitable coating to form. By comparison, the silyl ether-modified hydrophilic polymer can be applied to an inner surface of a device which is difficult or impossible to suitably irradiate, and the coated material can be dried, and then heated to cause hydrolysis of the silyl ether groups and covalent bonding to the surface and/or crosslinking to another coating material.

In one aspect, the invention provides an implantable or insertable medical device comprising a polymeric matrix, the polymeric matrix comprising a hydrophilic polymer having pendent groups comprising a reacted silyl ether group. In some aspects, the reacted silyl ether group bonds the hydrophilic polymer to a target material of the medical device. In some aspects, the matrix is in the form of a coating on the device surface. The reacted silyl ether group can be in the form of a siloxane group covalently linking the hydrophilic polymer to a device surface. Alternatively, or in addition, a siloxane group covalently links the hydrophilic polymer to another polymer. In some aspects, the device has an inner surface and the coating is formed on an inner surface of the device.

DETAILED DESCRIPTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The invention is generally directed to silyl ether-modified hydrophilic polymers, compositions including these polymers, and polymeric matrices (e.g., coatings) that are formed using these polymers. These silyl ether-modified hydrophilic polymers include pre-reacted polymers having one or more pendant group(s) comprising a reactive silyl ether group, as well as polymers with reacted silyl ether groups (i.e., in polymeric matrix form) where an ether group may no longer be present, but the silicon atom remains as a part of the formed matrix.

As used herein the term "silyl ether" refers to a silicon atom bonded to one or more carbon-containing groups via an oxygen atom (i.e., an ether linkage).

As used herein, the term "hydrophilic" refers to a polymer that is water-loving; typically, the hydrophilic polymers swell in the presence of water.

As used herein the term "polymer" refers to a compound having one or more of the same or different repeating monomeric units and includes linear homopolymers and copolymers, branched homopolymers and copolymers, graft homopolymers and copolymers, and the like. Polymers are typically formed by polymerization of monomers having polymerizable groups. A polymer therefore includes monomeric units and has a "polymeric backbone."

In some embodiments a coating is formed on an article wherein the hydrophilic polymer improves the lubricity of the article. As used herein, the term "lubricity" refers to a characterization of the frictional force associated with a coating. A coating with improved lubricity has a lower frictional force. Also, in many aspects, a coating is formed wherein the coating has improved durability. As used herein, the term "durability" refers to the wear resistance of a polymer coating, or the ability of a coating to adhere to an article surface when subjected to forces typically encountered during use (for example, normal force, shear force, and the like). A more durable coating is less easily removed from a substrate by abrasion. Durability of a coating can be assessed by subjecting the article to conditions that simulate use conditions.

In one aspect, durability can be measured by the ability of a coating to maintain a low friction surface after being repeatedly subjected to frictional forces. An initial test for durability may be performed by wetting the surface of the coated article (e.g., a coated catheter) and then repeatedly rubbing the article between two fingers along the length of the device to determine if any coating becomes removed, or if the coating looses its slipperiness after a number of rubs. A more quantitative analysis can be performed using mechanical equipment. For example, a "vertical pinch test" can be performed on the coated article, as described in International Application Number WO 03/055611. The coated article can be inserted into the end of a rod holder, which is placed between the two jaws of a pinch tester and immersed in a cylinder of water or saline. The jaws of the pinch tester are closed as the sample is pulled in a vertical direction and opened when the coated sample was returned to the original position. A 500 g force is applied as the coated substrates are pulled up through the pinched jaws. The pull force exerted on the substrate is then measured (grams). Pull force (g) is equal to the coefficient of friction (COF) multiplied by pinch force (g). The average frictional force is determined for 5 cycles while the coated substrates travel 10 cm at a travel rate of 1 cm/sec. As one test of durability, in a durable coating the frictional force does not increase by more than 25% from the starting frictional force (first cycle) to the fifth cycle under a load of 500 g at a travel rate of 1 cm/sec.

In many embodiments, the coated material including the reacted silyl ether-modified hydrophilic polymer adheres to the article surface sufficiently to withstand the effect of shear forces encountered during insertion and/or removal of the article, which could otherwise result in delamination of the coating from the body member.

The hydrophilic polymer that is used to form the silyl ether-modified hydrophilic polymer may be a synthetic hydrophilic homopolymer or synthetic hydrophilic copolymer. Suitable synthetic hydrophilic polymers may be prepared from any suitable monomers including, for example, acrylic monomers, vinyl monomers, ether monomers, or combinations of any one or more of these. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these.

Examples of polymers that can be formed from these monomers include poly(acrylamide), poly(meth)acrylamide, poly(vinylpyrrolidone), poly(acrylic acid), poly(ethylene glycol), poly(vinyl alcohol), and poly(HEMA). Representative examples of hydrophilic copolymers include, for example, methyl vinyl ether/maleic anhydride copolymers, vinyl pyrrolidone/methacrylamide copolymers, and vinyl pyrrolidone/acrylamide copolymers, and mixtures of any of these. In some preferred embodiments, the hydrophilic polymer is a vinyl pyrrolidone copolymer, an acrylamide copolymer, or vinyl pyrrolidone/(meth)acrylamide copolymer.

In many embodiments, the silyl ether-modified hydrophilic polymers are prepared from a hydrophilic polymer that has been functionalized to allow the introduction of silyl ether groups as pendant groups to the backbone of the hydrophilic polymer. After formation of the hydrophilic polymer, the polymer is modified with a compound to provide pendent groups along the polymer backbone, the pendent groups including a silyl ether group. In many embodiments, the silyl ether groups are attached to the hydrophilic polymer by reaction of pendant reactive groups (e.g., amine groups) on the hydrophilic polymer with a silyl ether-containing compound having a co-reactive group (i.e., a group such as an isocyanate that reacts with the pendant reactive groups on the hydrophilic polymer).

In many embodiments, the hydrophilic polymer comprises a free radically polymerized hydrophilic copolymer that includes at least one monomer species that allows silyl ether groups to be covalently attached as pendant groups to the copolymer backbone. For example, a monomer species having side chains bearing isocyanate-reactive groups may be included in the copolymer. When copolymerized with the other monomer(s), the isocyanate-reactive functional group provides a point of chemical attachment for the silyl ether compound. Examples of isocyanate-reactive groups include amines, alcohols, carboxylic acids, ureas, carbanates, amides, and isocynates (self condensation). Exemplary monomers useful for introducing isocyanate-reactive species include, for example, N-(3-aminopropyl)methacrylamide hydrochloride (APMA), N-(3-aminobutyl)methacrylamide hydrochloride, and 2-methylallylamine hydrochloride. APMA introduces a side chain with a terminal secondary amine into a hydrophilic copolymer.

In many embodiments, the silyl ether-modified hydrophilic polymer has the structure shown below.

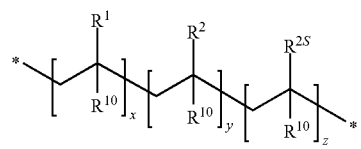

where $R^1$ is an organic side chain group;
$R^2$ is an organic side chain group that includes a reactive functional group (e.g., an amine) for attachment to a silyl ether group;
$R^{2S}$ is an $R^2$ side chain group that has been modified by the attachment of a silyl ether group;
$R^{10}$ is independently hydrogen or a lower alkyl group (e.g., methyl or ethyl); and
x, y, and z independently represent the amount of each species that is present in the polymer whether in random, block, or alternating configuration. Typically, x ranges from about 85 mole % to about 99 mole %, y ranges from 0 mole % to about 14 mole %, and z ranges from about 1 mole % to about 15 mole %.

Examples of common $R^1$ side chain groups include:

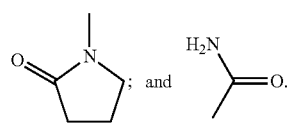

Examples of common $R^2$ side chain groups include:

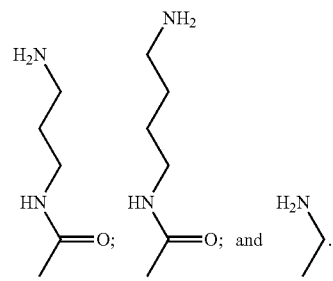

In many embodiments, $R^{2S}$ may be represented by the formula:

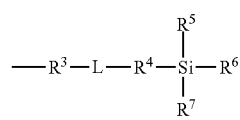

where L is a divalent linking group which may include C, H, O, or N atoms. Examples of common linking groups include urea groups (—NH—C(O)—NH—), and urethane groups (—NH—C(O)—O—);
$R^3$ is a side chain divalent segment, which may commonly include C, H, O, and N atoms; in some aspects $R^3$ is —(CO)NH(CH$_2$)$_n$—, and n is an integer in the range of 1-6; in some aspects m is 3 or 4;

R$^4$ is a side chain divalent segment, which may commonly include C, H, O, and N atoms; in some aspects R$^4$ is —(CH$_2$)$_n$—, and n is an integer in the range of 1-6; in some aspects n is 3 or 4;

R$^5$, R$^6$, and R$^7$ are independently selected from R$^8$ and OR$^8$, wherein R$^8$ includes a monovalent hydrocarbon group, such as a C1-C6-containing monovalent hydrocarbon group, or more specifically a linear or branched C1-C6 monovalent alkyl group, with the proviso that at least one of R$^5$, R$^6$, or R$^7$ is OR$^8$. In other specific aspects, all of R$^5$, R$^6$, and R$^7$, are independently selected from OR$^8$, wherein R$^8$ is a C1-C6-containing monovalent hydrocarbon group.

In an exemplary embodiment, the polymer backbone comprises a copolymer formed by copolymerizing vinyl pyrrolidone with N-(3-aminopropyl)methacrylamide. The resulting copolymer has the general structure shown below.

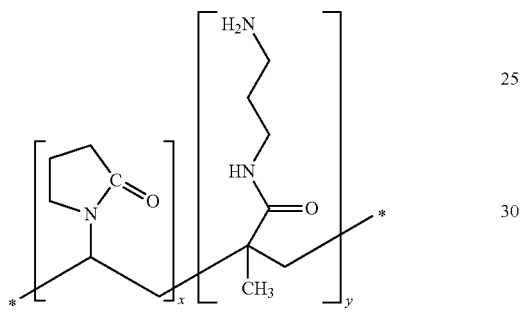

where x and y independently represent the amount of each monomer in the copolymer whether in random, block or alternating configuration. Typically, x ranges from about 85 mole % to 99 mole % and y ranges from about 1 mole % to 15 mole %.

In the above hydrophilic polymer, the pendant primary amine groups provide functionality for covalent attachment of silyl ether groups. For example, as shown below, the amine groups of the hydrophilic copolymer can be reacted with an isocyanate-functional silyl ether compound (e.g., 3-isocyanatopropyltriethoxysilane). The reaction of the isocyanate groups with the amine groups on the hydrophilic polymer results in the formation of a urea linkage that covalently bonds the silyl ether compound to the hydrophilic polymer. In order to preserve the isocyanate group, the reaction is typically run under anhydrous conditions.

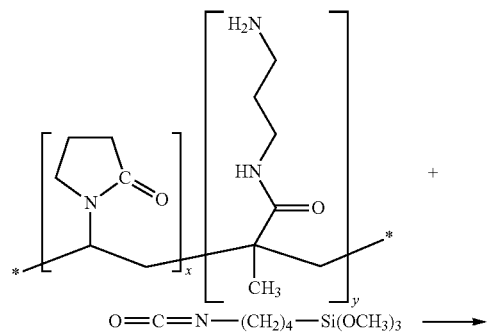

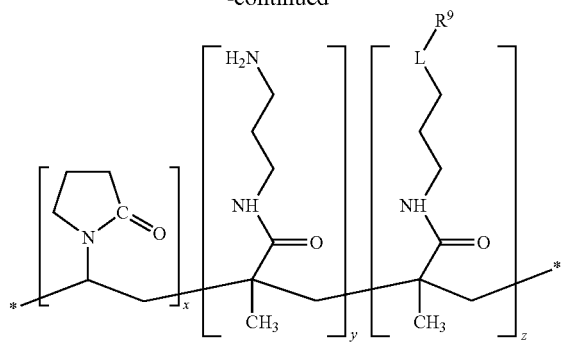

where L is —NH—C(O)—NH—;

R$^9$ is —(CH$_2$)$_4$—Si(OCH$_3$)$_3$; and x, y, and z independently represent the amount of each monomer in the copolymer whether in random, block or alternating configuration. Typically, x ranges from about 85 mole % to about 99 mole %; y ranges from 0 mole % to about 14 mole %; and z ranges from about 1 mole % to about 15 mole %.

In another exemplary embodiment, the polymer backbone comprises a copolymer formed by copolymerizing acrylamide with N-(3-aminopropyl)methacrylamide. The resulting copolymer has the general structure shown below.

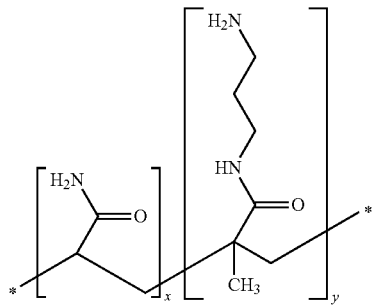

where x and y independently represent the amount of each monomer in the copolymer whether in random, block or alternating configuration. Typically, x ranges from about 85 mole % to about 99 mole % and y ranges from about 1 mole % to about 15 mole %.

In the hydrophilic polymer, the pendant primary amine groups provide functionality for covalent attachment of silyl ether groups onto the hydrophilic polymer. For example, as shown below, the amine groups of the hydrophilic copolymer can be reacted with an isocyanate-functional silyl ether compound (e.g., 3-isocyanatopropyltriethoxysilane). The reaction of the isocyanate groups with the amine groups on the hydrophilic polymer results in the formation of a urea linkage that covalently bonds the silyl ether compound to the hydrophilic polymer. In order to preserve the isocyanate group, the reaction is typically run under anhydrous conditions.

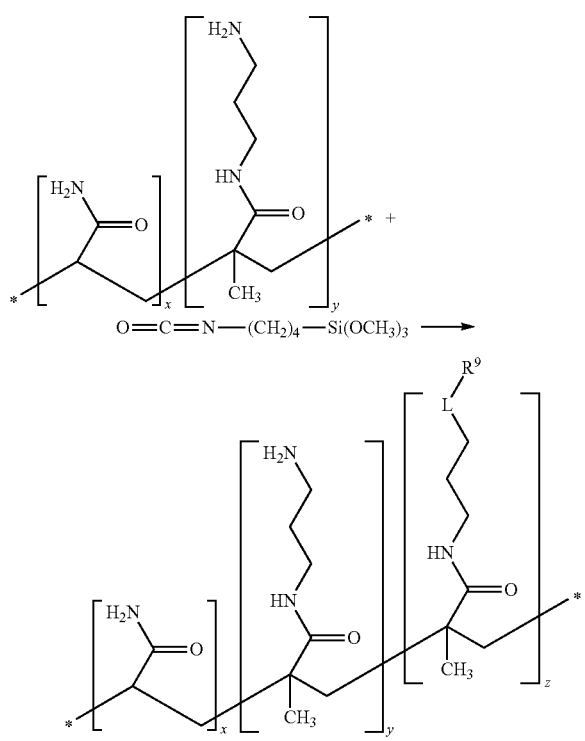

O=C=N—(CH$_2$)$_4$—Si(OCH$_3$)$_3$ ⟶ where

L is —NH—C(O)—NH—;

R$^9$ is —(CH$_2$)$_4$—Si(OCH$_3$)$_3$; and x, y, and z independently represent the amount of each monomer in the copolymer whether in random, block or alternating configuration. Typically, x ranges from about 85 mole % to about 99 mole %; y ranges from 0 mole % to about 14 mole %; and z ranges from about 1 mole % to about 15 mole %.

The number of silyl ether groups can be controlled, for example, by controlling the number of linking groups (e.g., primary amine groups) pendant from the hydrophilic polymer backbone. As the number of linking groups increase, the number of silyl ether groups in the resulting silyl ether modified hydrophilic polymer can also increase. It is also possible to control the number of silyl ether groups present in the silyl ether modified hydrophilic polymer by stoichiometrically limiting the silyl ether reactant. In this way, a portion of the reactive side chains are left unreacted in the silyl ether modified hydrophobic polymer. Typically, the hydrophilic polymer backbone includes less than about 15 mole % linking groups, for example, about 1 to about 15 mole % linking groups. The number of silyl ether groups can also be controlled, for example, by the number of reactive ether group(s) bonded to the silicon atom (i.e., the R$^5$, R$^6$, and R$^7$ groups) on the individual pendant group(s).

In an alternative mode of practice, the hydrophilic polymer is prepared by the copolymerization of a silyl ether-containing monomer with one or more other hydrophilic monomer(s). For example, the hydrophilic polymer can be formed by the free radical polymerization of a monomer composition that includes a free radically polymerizable silyl ether-containing monomer and a free radically polymerizable hydrophilic monomer that does not include a silyl ether group.

In one aspect, the silyl ether-containing monomer is of the formula:

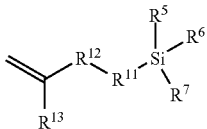

where

R$^5$, R$^6$, and R$^7$ are independently selected from R$^8$ and OR$^8$, wherein R$^8$ includes a monovalent hydrocarbon group, such as a C1-C6-containing monovalent hydrocarbon group, or more specifically a linear or branched C1-C6 monovalent alkyl group, with the proviso that at least one of R$^5$, R$^6$, or R$^7$ is OR$^8$. In other specific aspects, all of R$^5$, R$^6$, and R$^7$, are independently selected from OR$^8$, wherein R$^8$ is a C1-C6-containing monovalent hydrocarbon group, such as —CH$_3$, or —CH$_2$CH$_3$;

R$^{11}$ is a covalent bond (—) or —(CH$_2$)$_x$—, where x is an integer in the range of 1-6;

R$^{12}$ is a covalent bond (—) or —(CO)O—; and

R$^{13}$ is H, —CH$_3$, or —CH$_2$CH$_3$.

Examples of free radically polymerizable silyl ether-containing monomers include vinyltrimethoxysilane, allyltrimethoxysilane, triethoxyvinylsilane, 3-(trimethoxysilyl)propyl acrylate, allyltriethoxysilane, 3-(trimethoxysilyl)propyl methacrylate, trimethoxy(7-octen-1-yl)silane, and 3-(glycidyloxypropyl)triethoxysilane, which are commercially available, from, for example, Sigma Aldrich. Mixtures of two or more these monomers can also be used in the polymerization composition. Generally, the silyl ether-containing monomer is present in the polymerization mixture in a molar amount less than other hydrophilic monomer(s) that do not include a silyl ether group. In some preparations, the free radically polymerizable silyl ether-containing monomer, or combination of monomers, in the polymerization composition constitutes about 1-15 mole %, or about 2-10 mole % of the monomers in the mixture.

Exemplary monomers that do not include a silyl ether group and that can be used to prepare the hydrophilic polymer include, but are not limited to acrylic monomers and vinyl monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, aminopropylmethacrylamide (APMA), acrylamide-2-methylpropanesulfonic acid (AMPS), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Generally, one or a combination of these monomers is present in the polymerization mixture in a molar amount greater than the silyl ether-containing monomer(s). In some preparations, the monomer, or combination of monomers that do not include a silyl ether group, in the polymerization composition constitutes about 85-99 mole %, or about 90-98 mole % of the monomers in the mixture.

In many embodiments, the hydrophilic polymer formed by polymerization of a composition including a silyl ether-containing monomer and a monomer that does not include a silyl ether group has the structure shown below.

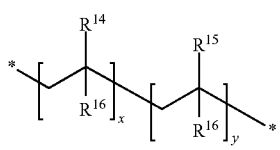

where $R^{14}$ is an organic side chain group;
$R^{15}$ is:

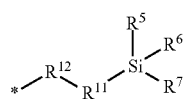

where $R^5$, $R^6$, and $R^7$ are independently selected from $R^8$ and $OR^8$, wherein $R^8$ includes a monovalent hydrocarbon group, such as a C1-C6-containing monovalent hydrocarbon group, or more specifically a linear or branched C1-C6 monovalent alkyl group, with the proviso that at least one of $R^5$, $R^6$, or $R^7$ is $OR^8$. In other specific aspects, all of $R^5$, $R^6$, and $R^7$, are independently selected from $OR^8$, wherein $R^8$ is a C1-C6-containing monovalent hydrocarbon group, such as —$CH_3$, or —$CH_2CH_3$;

$R^{11}$ is a covalent bond (—) or —$(CH_2)_x$—, where x is an integer in the range of 1-6;

$R^{12}$ is a covalent bond (—) or —(CO)O—; and $R^{16}$ is independently hydrogen or a lower alkyl group (e.g., methyl or ethyl); and x and y independently represent the amount of each species that is present in the polymer whether in random, block, or alternating configuration. Typically, x ranges from about 85 mole % to about 99 mole %, and y ranges from about 1 mole % to about 15 mole %.

In another exemplary embodiment, the hydrophilic polymer is formed by copolymerizing vinyl pyrrolidone with an allyl trialkyloxy silane monomer. The resulting copolymer has the general structure shown below.

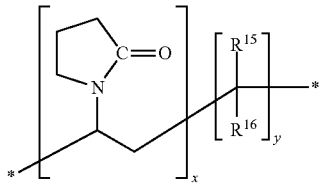

Where $R^{15}$ is:

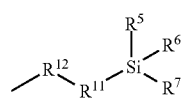

$R^{12}$ is a covalent bond, and $R^5$, $R^6$, $R^7$, $R^{11}$, and $R^{16}$ have the meanings described herein, and x and y independently represent the amount of each monomer in the copolymer whether in random, block or alternating configuration. Typically, x ranges from about 85 mole % to about 99 mole %; and y ranges from about 1 mole % to about 15 mole %.

The hydrophilic polymer that is formed (either by reaction of a hydrophilic prepolymer with a silyl ether-containing compound, or by the polymerization of a monomer mixture that includes a silyl ether-containing monomer) can also be described in terms of the amount of silyl ether group (mmol) pendent per gram of polymer. In some aspects, the amount of silyl ether group is in the range of about 0.05 mmol to about 1.5 mmol per gram of polymer, or about 0.15 mmol to about 0.75 mmol per gram of polymer.

Typically, the molecular weight of the hydrophilic polymer ranges from about 100,000 Da to 2,500,000 Da, and the molecular weight of the silyl ether-modified hydrophilic polymer ranges from about 102,000 Da to 3,250,000 Da, although other molecular weight species may also be useful.

As used herein a "polymeric matrix" refers to a mass of polymeric material that includes the silyl ether-modified hydrophilic polymer comprising a reacted silyl ether group. The polymeric matrix can be in various forms, such as in the form of a coating on a medical device, a filler material for a portion of a medical device, or a three-dimensional implant useful for a medical procedure. The reacted silyl ether group of the hydrophilic polymer in the polymeric matrix can be a part of a covalent bond between the hydrophilic polymer and a material of a medical device, a part of a covalent bond between the hydrophilic polymer and another polymer in the polymeric matrix, or both. For purposes of discussion, a polymeric matrix in the form of a coating on an implantable or insertable medical device is described.

The silyl ether-modified hydrophilic polymer of the invention can be utilized to coat any medical article for which it is desired to provide a lubricious coating on a surface thereof. In particular, the coatings are particularly useful for medical articles that can be inserted into and moved within the body. A coating formed using the silyl ether-modified hydrophilic polymer can be particularly useful for those devices that will come in contact with aqueous systems, such as bodily fluids. For example, a coated layer formed from the silyl ether-modified hydrophilic polymer can improve the lubricity of the surface and can facilitate movement of the device in the body.

Types of articles on which a coating containing the silyl ether-modified hydrophilic polymer can be formed are typically those that are introduced temporarily or permanently into a mammal for the prophylaxis or treatment of a medical condition. For example, these articles can be introduced subcutaneously, percutaneously or surgically to rest within an organ, tissue, or lumen of an organ, such as arteries, veins, ventricles, or atria of the heart.

In some aspects, a coating is formed by applying the silyl ether-modified hydrophilic polymer to a surface of a device and then treating the polymer to form a covalent bond to a target moiety via the activated silyl ether group. The material upon which the silyl ether-modified hydrophilic polymer is applied is reactive with hydrolyzed silyl ether group. The device can be formed of a material that inherently has groups that are able to bond with hydrolyzed silyl ether groups of the silyl ether-modified hydrophilic polymer.

Exemplary insertable or implantable medical devices include those that are partially or entirely made out of a metal or combination of metals. Although many devices or articles are constructed from substantially all metal materials, such as alloys, some may be constructed from both non-metal and metal materials, where at least a portion of the surface of the device is metal. The silyl ether-modified hydrophilic polymer can be bonded to a metal surface having oxidized metal atoms without requiring a tie layer material such as silane, polyurethane, or Parylene™.

A certain amount of oxidized metal species can be present at the device surface, providing reactive sites for an activated silyl-ether group of the polymer. Oxide or —OH groups on the metal surface allow the formation of siloxane bonds with the pendent group of the hydrophilic polymer. In some cases, the device can be pretreated to increase the amount of oxidized metal species on the device surface. For example, a metal device can be exposed to an environment enriched with oxygen to create more oxidized metal species. Oxidation of the metal surface can be promoted using a higher pressure and temperature.

Commonly used metals include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

A device surface can also be pretreated to introduce groups that are reactive with silyl ether groups. For example, some untreated metal surfaces will typically not be reactive with silyl ethers or silanols. The surface of devices made from such metals can be functionalized to provide groups that are able to react. In one mode of practice, the metal surface can be treated with a gas or a solution containing a base such as NaOH or KOH in a water or water/alcohol composition to create oxygen-containing groups on the device surface. Oxygen-containing functional groups such as —OH, —OOH, —CO, and —O can react with the silyl ether groups to provide a covalently bonded linkage between the device material and the silyl ether-modified hydrophilic polymer.

Also, although many articles are constructed from substantially all metal materials, such as alloys, some may be constructed from both non-metal and metal materials, where at least a portion of the surface of the article is metal. The metal surface may be a thin surface layer. Such surfaces can be formed by any method including sputter coating metal onto all or portions of the surface of the article.

In some aspects, a coating is formed by applying the silyl ether-modified hydrophilic polymer to a surface of a device that is made of a plastic and then treating the polymer to form a coating. Unexpectedly, the silyl ether-modified hydrophilic polymer was able to form a durable coating on a variety of different plastic substrates. Exemplary synthetic polymers, such as oligomers, homopolymers, and copolymers resulting from addition, condensation, or ring opening polymerizations can be a structural material of the device on which the coating is formed. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, and vinylidene difluoride. Examples of condensation or ring-opened polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone. In some cases the device is formed from a material selected from poly(etheresterketone) (PEEK), polyurethane, and Pebax.

The device may also be formed from halogenated polymers, such as Teflon™ and Neoflon™; polychlorotrifluoroethylene (PCTFE); fluorinated ethylene polymers (FEP), such as polymers of tetrafluoroethylene and hexafluoropropylene; poly(tetrafluoroethylene) (PTFE); and expanded poly (tetrafluoroethylene) (ePTFE).

Prior to disposing a coating composition containing the silyl ether-modified hydrophilic polymer on the surface of the article, the article may be cleaned using any suitable technique. For example, a cleaning process can include treating the surface using an alcohol such as isopropyl alcohol and then using a commercially available cleaning solution to further cleanse the surface.

The cleaning solution can also include a base (e.g., NaOH or KOH, as discussed herein) to create an oxidized metal surface. Exemplary cleaning solutions that have a high pH and that can be used to remove dirt and oil as well as to provide an oxide layer on a metal surface include Valtron™ SP2200 and Enprep™ 160SE.

Cleaning steps such as rinsing the article in distilled water or a different liquid, such as an alcohol, may be sufficient to clean the article according to the invention. Agitation or other mechanical action, such as sonication, may also be used in these cleaning processes.

Other device materials that a coating including the silyl ether-modified hydrophilic polymer can be formed on include non-metal surfaces that are reactive with the silyl ether-modified hydrophilic polymer of the present invention.

Other contemplated biomaterials include ceramics including, but not limited to, silicon nitride, silicon carbide, zirconia, and alumina, as well as glass, silica, and sapphire. Combinations of ceramics and metals can also be coated.

The type of device upon which a coating is formed can alternatively be described in terms of its configuration or architecture. For example, some exemplary insertable or implantable medical devices have a complex geometry, or an inner surface. "Inner surfaces" of devices are those surfaces in which only a limited amount of light, or no light, can be provided using conventional irradiation equipment. In other words, while conventional irradiation equipment can provide an ample amount of light to an outer surface of a device to immobilize a photoactivatable reagent, the same amount of light is not able to be provided to an inner surface to affect bonding and provide a comparable coated surface. Particular examples of substrates that have inner surfaces may include, for example, stents, catheters such as PTCA catheters and hemodialysis catheters, hemodialysis membranes, and other devices having inner surfaces. These substrates can be formed, for example, from a complex architecture of materials, may contain many pores, or have a lumen.

A device formed of a fabric, or that has fabric-like qualities, can reflect the complex geometry. The implantable device can be formed from textiles, which include woven materials, knitted materials, and braided materials. Particularly useful textile materials are woven materials which can be formed using any suitable weave pattern known in the art. The porous structure can be that of a graft, sheath, cover, patch, sleeve, wrap, casing, and the like, including many of the medical articles described herein. These types of articles can function as the medical article itself or be used in conjunction with another part of a medical article.

The silyl ether-modified hydrophilic polymer and methods described herein generally are beneficial for coating these types of surfaces as they may not require certain forms of energy, such as UV light, to activate and promote bonding of the polymeric material to form a coating on the surface. The inner surfaces of some implantable medical devices are often difficult to irradiate properly with UV light to affect bonding of reagents (e.g., photoactivatable reagents) to material surfaces. Use of the silyl ether-modified hydrophilic polymer is also advantageous over coatings formed by physical adsorption methods, as these may be less durable or have other undesirable characteristics, for example, flaking that may be exhibited over time. Therefore, use of silyl ether-modified hydrophilic polymer is advantageous as it can provide a uniform polymer coating to many substrates as well as substrates having complex geometries and inner surfaces.

A lubricious coating made using a silyl ether-modified hydrophilic polymer can also be formed on a surface of a catheter, including the external or internal walls of a catheter. The lubricious coating on both the internal and external portions of the catheter can improve function of the device. A coating on the external wall of the catheter can facilitate movement of the catheter within the lumen of the patient, reducing the frictional forces during the insertion process. A coating on the internal wall of the catheter can facilitate movement of a stent or a balloon that is movable within the lumen.

As another example, a lubricious coating made using a silyl ether-modified hydrophilic polymer can also be formed on a surface of an endoscopic sheath. Endoscopic sheaths are used in various medical procedures, including those involving the urogenital tract, the gastrointestinal tract, and the vasculature. In some arrangements, endoscopes are delivered through an endoscopic sheath in a medical procedure. A lubricious coating made using a silyl ether-modified hydrophilic polymer on the internal and external walls of the endoscopic sheath can facilitate movement of the sheath in the body and the device within the sheath.

Surfaces on which the silyl ether-modified hydrophilic polymer can be coated are not limited to those that are formed of metal, or that have inner surfaces or complex geometries. Other medical devices upon which a coating can be formed include vascular implants and grafts, grafts, surgical devices; synthetic prostheses; vascular prosthesis including endoprosthesis, small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuro-patches; orthopedic devices such as orthopedic joint implants, bone repair/augmentation devices, cartilage repair devices; urological devices and urethral devices such as urological implants, bladder devices, renal devices colostomy bag attachment devices; and biliary drainage products.

In order to form a coating, the silyl ether-modified hydrophilic polymer can be present in a liquid composition including a solvent suitable to dissolve the polymer. Examples of solvents that can be used to prepare a composition include polar liquids such as water, alcohols (e.g., methanol, ethanol, and isopropanol), and tetrahydrofuran (THF). Combinations of one or more of these or other polar liquids can also be used.

One preferred coating composition is an aqueous composition including water and an alcohol, such as isopropanol.

A coating composition is prepared using the silyl ether-modified hydrophilic polymer at a desired concentration. Useful polymer concentrations for forming a hydrophilic coating are in the range of about 0.1 mg/mL to about 50 mg/mL in an appropriate solvent or solvent combination. The type of polymeric backbone and liquid used to solvate the polymer can have an affect on the solubility of the polymer in the coating composition. The concentration of polymer used can affect coating properties, such as thickness and swellability. For example, thinner coated layers can be formed using coating composition having a lower concentration of the silyl ether-modified hydrophilic polymer.

Optionally, other polymeric materials, or non-polymeric materials can be included in the coating composition if desired. For example, the coating composition can include other water-soluble polymers that include chemistries that are reactive with an activated silyl ether group of the silyl ether-modified hydrophilic polymer, and/or water soluble non-polymeric materials, such as crosslinkers, that can be used to enhance the properties of the coating.

Optionally, crosslinkers including those having reactive silyl ether chemistries can be included in the polymer mixture, or used in the coating process, such as a primer coating. For example, a silyl ether-containing crosslinker can be included in the polymer coating composition, dried on the surface, and reacted to provide additional covalent bonding in the coating. This can enhance the durability of the coating. An exemplary silyl ether-containing crosslinker is 1,4-bis(triethoxysilyl)ethylbenzene.

Other optional crosslinkers that can be used to form a polymeric matrix include those having amine or hydroxyl groups, such as di- or tri-amines, or alcohols, such as polyols.

An exemplary coating composition includes the silyl ether-modified hydrophilic polymer, such as a silyl ether-modified vinyl pyrrolidone-methacrylamide copolymer dissolved in isopropyl alcohol at a concentration of about 20 mg/mL.

In a formed coating, the hydrophilic polymer with reacted silyl ether groups can be present in one or more coated layers on all or a portion of the surface of the device. A "coating" as used herein can include one or more "coated layers", each coated layer including one or more coating materials. In some cases, the coating can be formed of a single layer of material that includes the hydrophilic polymer. The single layer of material can include the hydrophilic polymer as the sole polymeric component, or the layer can include other polymeric components.

In other cases, the coating includes more than one coated layer, at least one of the coated layers including a reacted silyl ether-modified hydrophilic polymer. If more than one layer is present in the coating, the layers can be composed of the same or different materials.

Coatings can include base coats and top coats, which typically having certain physical and functional properties, such as thickness, permeability, strength, and protectivity. Optionally, the coating can include bioactive agents (such as pharmaceuticals) that can be eluted or that are immobilized in the coating to provide a beneficial effect, e.g. hemocompatibility.

In some aspects, a silyl ether group of the silyl ether-modified hydrophilic polymer is reacted with a material on the surface of article (such as a medical device) to form a coated layer, wherein the silyl ether-modified hydrophilic polymer becomes bonded to the material surface via a siloxane group. Alternatively, the device material can also include a polymeric base layer that provides hydroxyl functionalities thereby providing reactive sites for an activated silyl-ether group of the polymer.

For the formation of a coating, a solution containing the silyl ether-modified hydrophilic polymer can be applied to the device surface and allowed to react.

In some modes of practice, a coated layer containing a reacted silyl ether group of the silyl ether-modified hydrophilic polymer is formed. The bonding reaction can be carried out in aqueous conditions (for example, with the formation and hydrolysis of silanol groups), or in non-aqueous conditions. Bonding can proceed via a condensation reaction. For example, a composition (such as a solution) including the silyl ether-modified hydrophilic polymer is disposed on the surface, and the silyl ether groups hydrolyze and react with oxygen-containing groups on the device surface to form covalent siloxane bonds between the device surface and the hydrophilic polymer. Polymer-polymer crosslinking through reacted silyl ether groups may also occur. Therefore, the coated layer can include the hydrophilic polymer covalently bonded to the device surface via silane-containing groups, as well as crosslinked hydrophilic polymer wherein the crosslinking occurs through pendent reacted silane-containing groups of the hydrophilic polymer.

A coating composition including the silyl ether-modified hydrophilic polymer can be applied to a medical device using standard techniques to cover the entire surface of the device, or a portion of the device surface. If more than one coated layer is applied to a surface, it is typically applied successively. For example, a coated layer can be formed by applying the coating composition using a technique such as immersion, dipping, spraying, brushing, or swabbing.

For example, a typical dip-coating procedure involves immersing the article to be coated in the coating composition containing the silyl ether-modified hydrophilic polymer, dwelling the object in the composition for a period of time (a standard time is generally about 30 seconds or less, and can even be less that 10 seconds in many cases, but can also be soaked for longer times, such as a number of minues), and then removing the article from the composition. After the article has been dip-coated in the coating solution, it is removed and dried. Drying can be carried out using any suitable method, including air-drying the dip coated article. Times up to 30 minutes can be sufficient to dry the coated article although shorter times may be also sufficient.

Alternatively, the coating composition can be spray coated onto the surface of the article. An exemplary spray coating process and apparatus that can be used for coating implantable medical articles using the compositions of the present invention is described in U.S. Pat. No. 7,192,484 (Chappa et al.). Application of the coating composition using such a spray coating technique can facilitate the rapid drying of the composition on the device surface.

The polymer can then be heated to promote reaction of the silyl ether group and covalent bond formation with a target. In some cases, the process can be repeated to provide a coating having multiple coated layers, wherein at least one layer includes the reacted silyl ether-modified hydrophilic polymer. For example, two or three successive coatings of hydrophilic polymer can be applied to the surface.

In one particular mode of practice, the polymer-containing solution is applied to an inner surface of a medical device, such as one made from metal, glass, plastic, or ceramic, using a syringe. The inner surface of the medical device comprises a tubular or cylindrical shape and the solution is applied at least to the inner surface of the tube or cylinder. Application of the coating solution can result in the silyl ether-modified hydrophilic polymer being deposited on the surface of the device.

Excess coating solution can be removed from the device surface by a process such as air flow. Once the silyl ether-modified hydrophilic polymer has been dried on the surface, the device can be heated to promote bonding of the polymer to the device surface, and/or to another hydrophilic polymer, via reaction of the silyl ether. In an exemplary mode of practice the coated device is heated to a temperature of about 50° C. or greater, such as about 60° C., for a period of time of about two hours or greater, such as for a period of time in the range of about 4-16 hours. In another exemplary mode of practice the coated device is heated to a temperature of about 100° C. or greater, such as about 110° C. for a shorter period of time, such as about 10 minutes to about 30 minutes, for example, about 15 minutes. Treatment at lower temperatures for a longer period of time is recommended for articles made of softer plastics that may otherwise deform at higher temperatures.

Hydrophilic gels formed using the silyl ether-modified hydrophilic polymers of the invention can be used, for example, as filter materials for implantable objects (such as surgical meshes), as adhesive gels for medical devices, such as electrodes, or as occlusive articles for use in the body (in vivo) or on the body (e.g., for dermal treatment). The silyl ether-modified hydrophilic polymers can also be used to form molded articles such as contact lenses.

As an example, a composition including a silyl ether-modified hydrophilic polymer can be disposed in a mold and treated to form a crosslinked hydrogel article. The composition can be treated to reduce water content, and then heated to affect polymer crosslinking and cure the composition. Optionally, the composition can include crosslinking reagents, such as non-polymeric silane-based crosslinking reagents.

In some aspects, a coating can be formed that includes the following formula:

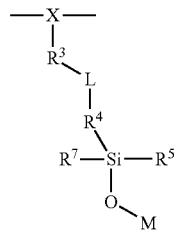

In the formula above, M represents an atom of the substrate material, or an atom of another polymer in a coating; X represents an atom in the polymer backbone of the hydrophilic polymer; and L, $R^3$, $R^4$, $R^5$, and $R^7$ are as described hereinabove. In some aspects M is an atom of a metal, glass, or plastic substrate.

In some aspects, a coating can be formed that includes the following formula:

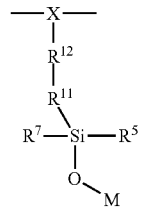

In the formula above, M represents an atom of the substrate material, or an atom of another polymer in a coating; X represents an atom in the polymer backbone of the hydrophilic polymer; and $R^5$, $R^7$, $R^{11}$, and $R^{12}$ are as described hereinabove. In some aspects M is an atom of a metal, glass, or plastic substrate.

Optionally, in addition to the pendent silane-containing group bonding the polymer to the substrate material, the coating may also include polymer-polymer crosslinking. Optional polymer-polymer crosslinking can be established by condensation reaction between the silyl ether, resulting in covalent bonding via pendent silane-containing groups.

In some aspects, silyl ether groups of the silyl ether-modified hydrophilic polymer are reacted to crosslink the hydrophilic polymer via a siloxane linkage. This can be useful for formation of coatings and also various implants, and silane bonding to a different substrate material is not required.

Crosslinking can occur by hydrolysis of a silyl ether group, and subsequent reaction with a silane group through a condensation reaction. Silane-containing groups associate by hydrogen bonding, and then an increase in temperature can promote the condensation reaction. Crosslinking can also occur through formation of silanol group following loss of the alkyl radical, and subsequent reaction with a silane group accompanies loss of a water molecule. The extent of crosslinking can be modulated by the reaction conditions including time, heat, etc.

In some aspects, a coating can be formed that includes the following formula:

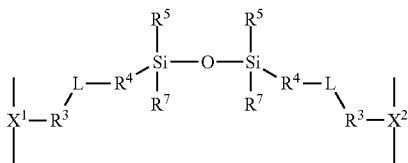

In the formula above, $X^1$ and $X^2$ represent monomeric units of different hydrophilic polymers, and L, $R^3$, $R^4$, $R^5$, and $R^7$ are as described hereinabove. The formula above exemplifies the crosslinking of two silyl ether-modified hydrophilic polymers through their respective monomeric unit via a crosslinking chemistry.

In some aspects, a coating can be formed that includes the following formula:

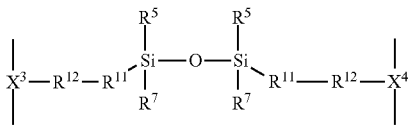

In the formula above, $X^3$ and $X^4$ represent monomeric units of different hydrophilic polymers, and $R^5$, $R^7$, $R^{11}$, and $R^{12}$ are as described hereinabove. The formula above exemplifies the crosslinking of two silyl ether-modified hydrophilic polymers through their respective monomeric unit via a crosslinking chemistry.

Medical articles associated with a matrix formed from the silyl ether-modified hydrophilic polymer can be treated to sterilize one or more parts of the article, or the entire medical article. Sterilization can take place prior to using the medical article and/or, in some cases, during implantation of the medical article.

Optionally, a coating capable of releasing a bioactive agent is formed on the surface of a medical device. One or more bioactive agents may be present in the coating. A bioactive agent that is present in and capable of being released from the coating can be present in a coated layer formed from the silyl ether-modified hydrophilic polymer, or can be present in a different coated layer, such as one that is formed from other polymeric material. For example, the silyl ether-modified hydrophilic polymer may be present as a top coat, and a base or intermediate coated layer that is between the top coat and the device surface can include a bioactive agent. The bioactive agent can be released from the base or intermediate coated layer and through the top coat.

Alternatively the coating includes an immobilized bioactive agent. For example, a bioactive agent can be covalently or ionically bonded to a component in the coating, and the presence of the bioactive agent can provide an additional property in addition to the lubricity provided by the silyl ether-modified hydrophilic polymer.

The term "bioactive agent," refers to an inorganic or organic molecule, which can be synthetic or natural, that causes a biological effect when administered in vivo to an animal, including but not limited to birds and mammals, including humans.

A partial list of bioactive agents is provided below. According to embodiments of the present invention, one may choose one or more of the bioactive agents to be included in a coating is formed from the silyl ether-modified hydrophilic polymer. A comprehensive listing of bioactive agents, in addition to information of the water solubility of the bioactive agents, can be found in The Merck Index Fourteenth Edition, Merck & Co. (2006).

Bioactive agents can fall within one or more of the following bioactive agent classes. These classes include, but are not limited to: ACE inhibitors, actin inhibitors, analgesics, anesthetics, anti-hypertensives, anti polymerases, antisecretory agents, anti-AIDS substances, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

Improved lubricity of a coated surface can be shown by a reduction in the water contact angle on polymer-coated surfaces in comparison to uncoated surfaces. Reduction of water contact angle is indicative of increased wettability, which associates with an improvement in lubricity. In addition to providing improved lubricity to a surface, the coatings can also be more durable due to the bonding of the reacted silyl ether groups. As such, the coatings can demonstrate good lubricity following physical challenge.

The invention will be further described with reference to the following non-limiting Examples.

EXAMPLE 1

Preparation of poly[vinyl pyrrolidone-co-N-(3-aminopropyl)methacrylamide]

N-(3-aminopropyl)methacrylamide hydrochloride (0.63 g), vinyl pyrrolidone (10.05 g) and tetramethylethylenediamine (0.091 g; TEMED) were placed in an amber bottle (250 mL). Deionized water (156 mL) was added to the reaction mixture and it was purged with nitrogen. After 10 minutes of purging, azobisisobutyronitrile (0.173 g; AIBN) was added and the reaction mixture was shaken at 50° C. After 16 hours of heating, viscous mixture was placed into 12,000-14,000 MWCO dialysis tubing and dialyzed against water for 5 days at room temperature. Product was lyophilized and 12.26 g of white solid was obtained.

EXAMPLE 2

Preparation of poly[vinyl pyrrolidone-co-N—(N-propyltriethoxysilane-N'-propylurea)methacrylamide]

Poly[vinyl pyrrolidone-co-N-(3-aminopropyl)methacrylamide] (1 g) was dissolved in $CH_2Cl_2$ (80 mL) for 30 minutes at room temperature under the inert atmosphere. 3-isocyanatopropyltriethoxysilane (0.05 g) was added to the reaction mixture. After 16 hours of stirring under inert atmosphere and at room temperature, solvent was removed and resulting white powder was dried in vacuo.

EXAMPLE 3

Inner Diameter Coating Process Using Silane Functionalized Polymer

Poly[vinyl pyrrolidone-co-N—(N-propyltriethoxysilane-N'-propylurea)methacrylamide] is dissolved in isopropyl alcohol (20 mg/mL). The solution is applied to the inner diameter of metal, glass or ceramic tube using syringe. Steady flow of air is passed through the tube to blow remaining solution out and dry the coating. Once the inner diameter is dry, the part is placed in a 60° C. vacuum oven for a period of time (4-16 hours) to allow silane to cure.

EXAMPLE 4

Preparation of poly[vinyl pyrrolidone-co-allyl-triethoxysilane]

Vinyl pyrrolidone (10.84 g) and allyl-triethoxysilane (0.51 g; Sigma Aldrich) are placed in a glass flask. Tetrahydrofuran is added to the reaction mixture and it is purged with nitrogen. After purging, 0.175 g of AIBN and 0.09 g of TEMED are added and the reaction mixture was shaken at 50° C. for about 16 hours. After polymerization, the polymer product is placed into 12,000-14,000 MWCO dialysis tubing and dialyzed against water for 5 days at room temperature. After dialysis, the polymer product is lyophilized.

EXAMPLE 5

Poly(vinylpyrrolidone)-silane coatings

An aqueous coating composition was prepared by dissolving poly(vinyl-pyrrolidone)-silane (as prepared in Example 2) at 5 mg/mL in water for 2 days with shaking at room temperature. The composition was used to coat ENPREP™-cleaned stainless steel flats, and Valtron-cleaned silicon wafer sections, and glass test tubes. Stainless steel flats were soaked in a cleansing solution of ENPREP™ (ENTHOME-OMI, Inc.) at a concentration of 60 mg/mL in DI water at a temperature of approximately 80° C. for approximately 1 hour. After soaking, the substrates were rinsed twice in distilled water for about 10 seconds each and then rinsed with IPA twice for 10 seconds each.

Coatings were formed by successively soaking the substrates in the coating solution, air drying the applied coating materials, and then baking the dried coating materials, three times. For the first coat, substrates were soaked for 5 minutes in the coating solution, air dried for 20 minutes (both at room temperature—~20° C.), and then baked for 15-20 minutes at 110° C. The second and third coats were soaked for 30 seconds in the coating solution at room temperature, and then dried and baked using the same conditions that followed first coat.

The coatings were slippery and very durable. To assess durability, the coated substrates were immersed in a Congo Red solution (3.5 mg/mL in water). The Congo Red-stained coated substrates were then rinsed with water to remove excess dye, upon which they also became lubricious. The substrates were then subjected to a manual durability test by rubbing 40 times between two fingers of a gloved hand. After 40 rubs the coating was visualized and was found to remain intact.

The poly(vinyl-pyrrolidone)-silane coating composition (5 mg/mL) PVP-silane was also used to coat plastics. Four sets of different plastic samples were coated. These coated samples were (a) a poly(etheresterketone) (PEEK) rod, (b) a clear polyurethane (PU) rod, (c) a white soft Pebax rod, and (d) dark blue Pebax rod. Plastic substrates were cleaned in isopropanol (IPA).

Coatings on the plastic substrates were formed by successively soaking the substrates in the coating solution, air drying the applied coating materials, and then baking the dried coating materials, two times. For the first and second coats, substrates were soaked for 30 seconds in the coating solution and air dried for 10 minutes (both at room temperature), and then baked for 15 minutes at 110° C.

To assess durability, the coated substrates were stained with Congo Red solution and then subjected to durability testing as described with the non-plastic coated substrates. The coatings on the plastic substrates were slippery and substantially durable (40+ rubs).

As a control, a commercially available poly(vinyl-pyrrolidone) (without silane groups) was used in a method in an attempt to coat the plastics, metal, glass substrates. However, the resulting coatings rinsed off under water flow and did not require rubbing for their removal.

EXAMPLE 6

Poly(vinylpyrrolidone)-silane Coatings

A solution of poly(vinyl-pyrrolidone)-silane (as prepared in Example 2) at 5 mg/mL in 50% IPA/50% water was prepared. Coatings on bare metal substrates (ENPREP™ cleaned) using 30-40 minute bakes at 110° C. (single coated layer) resulted in durable and lubricious coatings.

The use of an organic solvent such as IPA allowed the solution to coat the substrate more effectively.

Samples of PEEK and blue PEBAX rods were coated with 3 coats, machine dipped at 0.4 cm/s with 30 second dwell time in the coating solution. Each coat was air dried and then baked at 110° C. for 35 minutes.

What is claimed is:

1. An implantable or insertable medical device comprising a polymeric matrix, the polymeric matrix comprising a hydrophilic polymer having pendent groups comprising a reacted silyl ether group, the matrix formed from an aqueous composition comprising hydrophilic polymer having the formula:

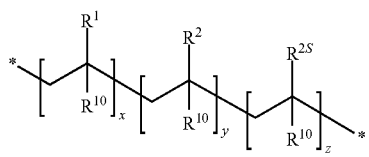

where $R^1$ comprises an organic side chain group selected from

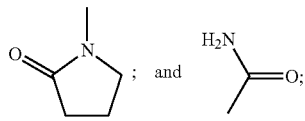

$R^2$ comprises an amine group;
$R^{2S}$ comprises a silyl ether group;
$R^{10}$ is independently hydrogen, methyl, or ethyl; and
wherein x, y, and z independently represent the amount of each monomer species present in the polymer in random, block, or alternating configuration, with x in the range of 85 mole % to 99 mole %, y in the range of 0 mole % to 14 mole %, and z in the range of 1 mole % to 15 mole %; and wherein
the hydrophilic polymer is present at a concentration in the range of 0.1 mg/mL to 50 mg/mL in the aqueous composition.

2. The device of claim 1 where the reacted silyl ether group has the following formula:

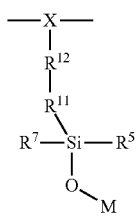

where M represents an atom of material of the device the polymeric matrix is in contact with, or an atom of another polymer in the matrix; X represents an atom in the polymer backbone of the hydrophilic polymer; side chain divalent segment, having one or more of C, H, O, or N", and substitute therefor "L is selected from —NH—C(O)—NH— or —NH—C(O)—O—; $R^3$ is —(CO)NH(CH$_2$)$_m$—, and m is an integer in the range of 1-6; $R^4$ is —(CH$_2$)$_n$—, and n is an integer in the range of 1-6"; $R^5$ and $R^7$ are independently selected from $R^8$ and OR$^8$, wherein $R^8$ is a C1-C6-containing monovalent alkyl group.

3. The device of claim 2 wherein n is 3 or 4.

4. The device of claim 2 wherein m is 3 or 4.

5. The device of claim 1 where $R^{2S}$ is

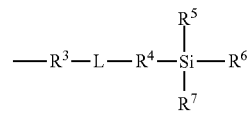

wherein
$R^3$ is —(CO)NH(CH$_2$)$_m$—, and m is an integer in the range of 1-6;
L is selected from —NH—C(O)—NH— and —NH—C(O)—O—;
$R^4$ is —(CH$_2$)$_n$—, and n is an integer in the range of 1-6;
$R^5$, $R^6$, and $R^7$ are independently selected from $R^8$ and OR$^8$, wherein $R^8$ is a linear or branched C1-C6 monovalent alkyl group, with the proviso that at least one of $R^5$, $R^6$, or $R^7$ is OR$^8$.

6. The device of claim 1 which is a catheter.

7. The device of claim 1 wherein the polymeric matrix is present on an inner surface of the device.

8. A method for providing a coating to an implantable or insertable medical device comprising steps of
applying an aqueous composition to a surface of the device, the aqueous composition comprising a hydrophilic polymer comprising a pendent group comprising a reactive silyl ether group, the hydrophilic polymer having the formula:

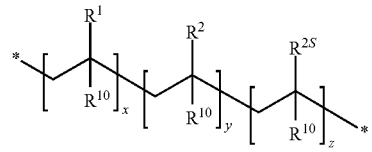

where $R^1$ comprises an organic side chain group selected from

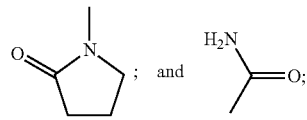

$R^2$ comprises an amine group;
$R^{2S}$ comprises a silyl ether group;
$R^{10}$ is independently hydrogen, methyl, or ethyl; and
wherein x, y, and z independently represent the amount of each monomer species present in the polymer in random, block, or alternating configuration, with x in the range of 85 mole % to 99 mole %, y in the range of 0 mole % to 14 mole %, and z in the range of 1 mole % to 15 mole %; and present at a concentration in the range of 0.1 mg/mL to 50 mg/mL in the aqueous composition; and
heating the hydrophilic polymer to cause reaction of the silyl ether group and covalent bonding of the polymer to the surface or the device or to another hydrophilic polymer.

9. The method of claim 8 wherein the composition is an aqueous composition optionally including an alcohol.

10. The method of claim 8 wherein the method comprises a step of drying the composition on the device surface to remove liquid.

11. The method of claim 8 wherein the step of heating is performed at 100° C. or greater.

12. The device of claim 1 wherein the aqueous composition comprises a mixture of (a) water and (b) an alcohol or tetrahydrofuran.

13. An implantable or insertable medical device comprising a polymeric matrix, the polymeric matrix comprising a hydrophilic polymer having pendent groups comprising a reacted silyl ether group, wherein the polymeric matrix is formed by a polymer having the formula:

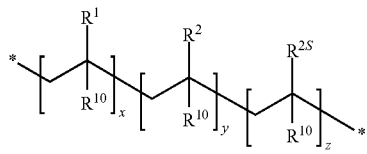

where
$R^1$ comprises an organic side chain group selected from

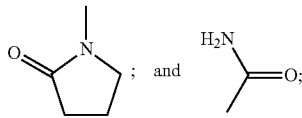

$R^2$ comprises an amine group;
$R^{2S}$ comprises a silyl ether group;
$R^{10}$ is independently hydrogen, methyl, or ethyl; and
wherein x, y, and z independently represent the amount of each monomer species present in the polymer in random, block, or alternating configuration, with x in the range of 85 mole % to 99 mole %, y in the range of 0 mole % to 14 mole %, and z in the range of 1 mole % to 15 mole %.

14. The device of claim 13 which is a catheter, and the polymeric matrix comprises a coating on a surface of the catheter.

15. The device of claim 13 wherein the polymeric matrix is present on an inner surface of the device.

16. An implantable or insertable medical device comprising a polymeric matrix, the polymeric matrix comprising a hydrophilic polymer having pendent groups comprising a reacted silyl ether group, wherein the polymeric matrix is formed by a polymer having the formula:

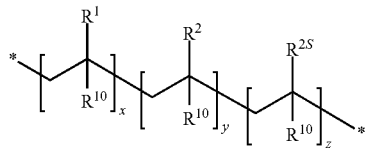

where
$R^1$ comprises an organic side chain group;
$R^2$ comprises an amine group;
$R^{2S}$ is

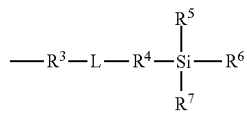

wherein
$R^3$ is $-(CO)NH(CH_2)_m-$, and m is an integer in the range of 1-6;
L is selected from $-NH-C(O)-NH-$ and $-NH-C(O)-O-$;
$R^4$ is $-(CH_2)_n-$, and n is an integer in the range of 1-6;
$R^5$, $R^6$, and $R^7$ are independently selected from $R^8$ and $OR^8$, wherein $R^8$ is a linear or branched C1-C6 monovalent alkyl group, with the proviso that at least one of $R^5$, $R^6$, or $R^7$ is $OR^8$;
$R^{10}$ is independently hydrogen, methyl, or ethyl; and
wherein x, y, and z independently represent the amount of each monomer species present in the polymer in random, block, or alternating configuration, with x in the range of 85 mole % to 99 mole %, y in the range of 0 mole % to 14 mole %, and z in the range of 1 mole % to 15 mole %.

17. The device of claim 16 which is a catheter, and the polymeric matrix comprises a coating on a surface of the catheter.

18. The device of claim 16 wherein the polymeric matrix is present on an inner surface of the device.

* * * * *

UNITED STATES PATENT AND TRADEMARK OFFICE
CERTIFICATE OF CORRECTION

PATENT NO.         : 8,475,843 B2
APPLICATION NO.    : 12/981885
DATED              : July 2, 2013
INVENTOR(S)        : Aleksey V. Kurdyumov, Robert Hergenrother and Bruce M. Jelle Page 1 of 2

It is certified that error appears in the above-identified patent and that said Letters Patent is hereby corrected as shown below:

In the Claims:

- Column 23, Claim 2, Lines 45-55, Figure, " 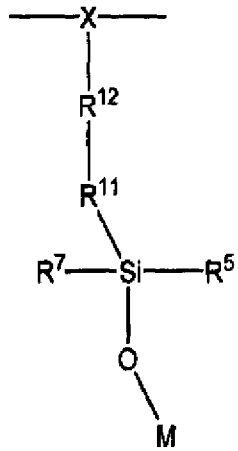 " should be 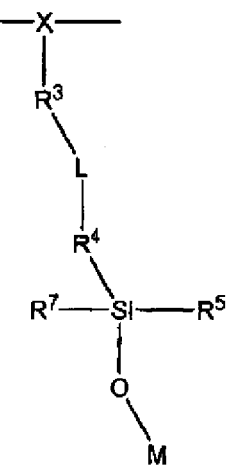

Signed and Sealed this
Twenty-sixth Day of November, 2013

Margaret A. Focarino
*Commissioner for Patents of the United States Patent and Trademark Office*

- Column 23, Claim 2, lines 58-63, "side chain divalent segment, having one or more of C, H, O, or N", and substitute therefor" should be -- L is selected from –NH-C(O)-NH- or –NH-C(O)-O-; $R^3$ is –(CO)NH(CH$_2$)$_m$-, and $m$ is an integer in the range of 1-6; $R^4$ is –(CH$_2$)$_n$-, and $n$ is an integer in the range of 1-6; --